(12) United States Patent
Shedlov et al.

(10) Patent No.: US 7,589,297 B2
(45) Date of Patent: Sep. 15, 2009

(54) APPARATUS AND METHOD FOR CUTTING FLAT STENT PRECURSORS

(75) Inventors: Matthew Shedlov, Rockford, MN (US); Brian J. Hanson, Little Canada, MN (US); Kevin K. King, Maple Grove, MN (US); David D. Groneberg, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 600 days.

(21) Appl. No.: 11/297,499

(22) Filed: Dec. 8, 2005

(65) Prior Publication Data

US 2007/0131662 A1    Jun. 14, 2007

(51) Int. Cl.
*B23K 26/38* (2006.01)
*B23K 26/08* (2006.01)

(52) U.S. Cl. .................. 219/121.67; 219/121.82; 269/20

(58) Field of Classification Search ............ 219/121.67, 219/121.82, 121.84; 83/98, 99, 100; 226/97.1, 226/97.3, 97.4; 269/20, 21, 27
See application file for complete search history.

(56) References Cited

U.S. PATENT DOCUMENTS

| | | | |
|---|---|---|---|
| 3,622,058 A * | 11/1971 | Vits | ............ 226/97.3 |
| 4,403,134 A | 9/1983 | Klingel | |
| 5,773,791 A | 6/1998 | Kuykendal | |
| 6,888,098 B1 | 5/2005 | Merdan et al. | |
| 7,275,749 B2 * | 10/2007 | Matsuzawa et al. | ............ 269/21 |
| 2002/0091441 A1 | 7/2002 | Guzik | |
| 2004/0220658 A1* | 11/2004 | Limon | .............. 623/1.15 |

FOREIGN PATENT DOCUMENTS

| | | | |
|---|---|---|---|
| FR | 532728 | | 2/1922 |
| GB | 2 239 206 A1 | | 6/1991 |
| JP | 60-072666 | | 4/1985 |
| JP | 2-155588 A | * | 6/1990 |
| JP | 4-367384 A | * | 12/1992 |
| JP | 5-329678 A | * | 12/1993 |
| JP | 6-63785 A | * | 3/1994 |
| JP | 2002-283088 A | * | 10/2002 |
| JP | 2004-160495 A | * | 6/2004 |
| JP | 2004-186635 A | * | 7/2004 |

* cited by examiner

*Primary Examiner*—Geoffrey S Evans
(74) *Attorney, Agent, or Firm*—Crompton, Seager & Tufte LLC

(57) ABSTRACT

An apparatus for cutting a planar medical component having a first surface and a second surface, comprising a clamp for fixing the component and applying a tensile force, a support having a surface having a hole therein, the upper surface disposed proximate the second surface of the component, and a cutting device having a cutting head disposed proximate the support and facing the first surface, wherein the support is configured to move along the plane of the component relative to the clamp and the cutting device cutting head is configured to hold position relative to the support.

47 Claims, 15 Drawing Sheets

APPARATUS AND METHOD FOR CUTTING FLAT STENT PRECURSORS

FIELD

This invention pertains generally to processing flat medical components such as a stent precursor and more specifically to laser processing flat medical components using a support system.

BACKGROUND

Processing of medical components such as stents by laser cutting is known in the art. In some cases, a thin walled tube is laser cut to the desired configuration. In other cases, a flat piece of material such as a metallic material is first cut and then formed into a tubular stent. Stents comprises an interconnected lattice of struts that can expand into a mesh support tube. Processing a stent requires precise, smooth cuts. The present invention provides an improved manufacturing process for manufacturing medical devices such as stents.

SUMMARY

One embodiment pertains to a system for laser processing flat medical components such as stents. The system includes a component to tension the flat medical component such as clamps to hold material, which may be mounted on a linear slide such that tension may be applied to the workpiece, a tensioning device, a cutting nozzle and a center tower support. The center tower support is configured to be under the flat medical component to support it against the forces generated by the cutting nozzle. The center tower support has an upper surface support for supporting the workpiece and a center lumen. The center tower support may also be configured to be used with a fluid such as a lubrication fluid or a cooling fluid. In one such configuration, the center tower support includes an inner support tower having an annular upper surface and an outer support tower having an annular upper surface. The outer support tower and the inner support tower define a second, cylindrical lumen. Fluid may be provided either through the center lumen or the cylindrical lumen and may be evacuated through the other lumen or outwardly. The relative heights of the inner and outer support towers may be adjusted to control fluid flow direction and amount.

Another embodiment pertains to a center tower support insert that is configured to provide a liquid bearing surface. The insert has an annular, crowned shape that include fluid lumens having exit orifices on the upper surface of the insert. When fluid is provided through these lumens, a liquid bearing surface may be created.

Another embodiment pertains to an insert where a liquid bearing surface is created by the top surface of a weir in the insert. The weir is defined by an outer and inner wall, which capture the fluid and control the fluid flow direction. The top surface of the fluid in the weir may be used to support the workpiece.

Another embodiment pertains to a system for laser processing flat medical components where the center tower support and the cutting nozzle are held stationary and the flat medical component is moved laterally along the x-axis and the y-axis.

Another embodiment pertains to a system where the flat medical component is held stationary and the center tower support and the cutting nozzle are moved. The center tower support and the cutting nozzle may be mechanically synchronized by, for example, mounting them on separate arms of a cantilever.

Another embodiment pertains to a method of positioning the flat medical component in the clamps. Slits are provided in the component in a direction perpendicular to the direction of the tension. The slits may be positioned at first and second ends of the area of the component to be made into the part.

It is to be understood that both the foregoing general description and the following detailed description are exemplary, but not restrictive, of the invention.

DESCRIPTION OF DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION

The invention will next be illustrated with reference to the figures wherein the same numbers indicate similar elements in all figures. Such figures are intended to be illustrative rather than limiting and are included herewith to facilitate the explanation of the apparatus of the present invention.

Figure 1:
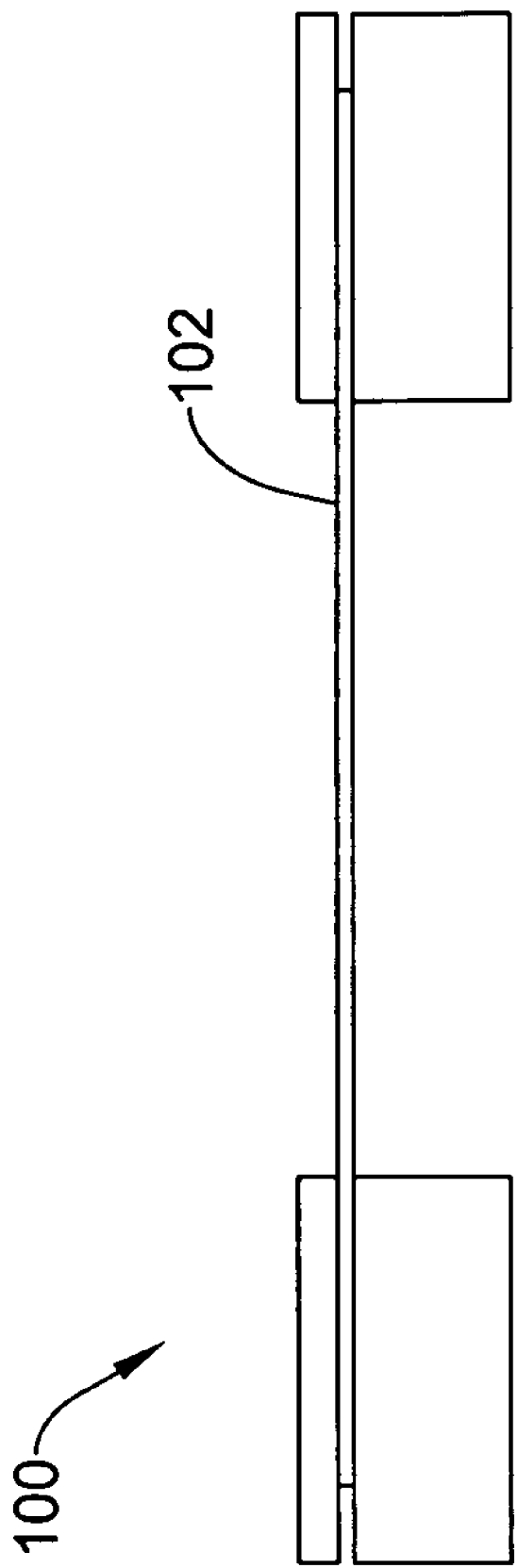
FIG. 1 is a plan view of a prior art support system for processing a flat stent.
Figure 2:
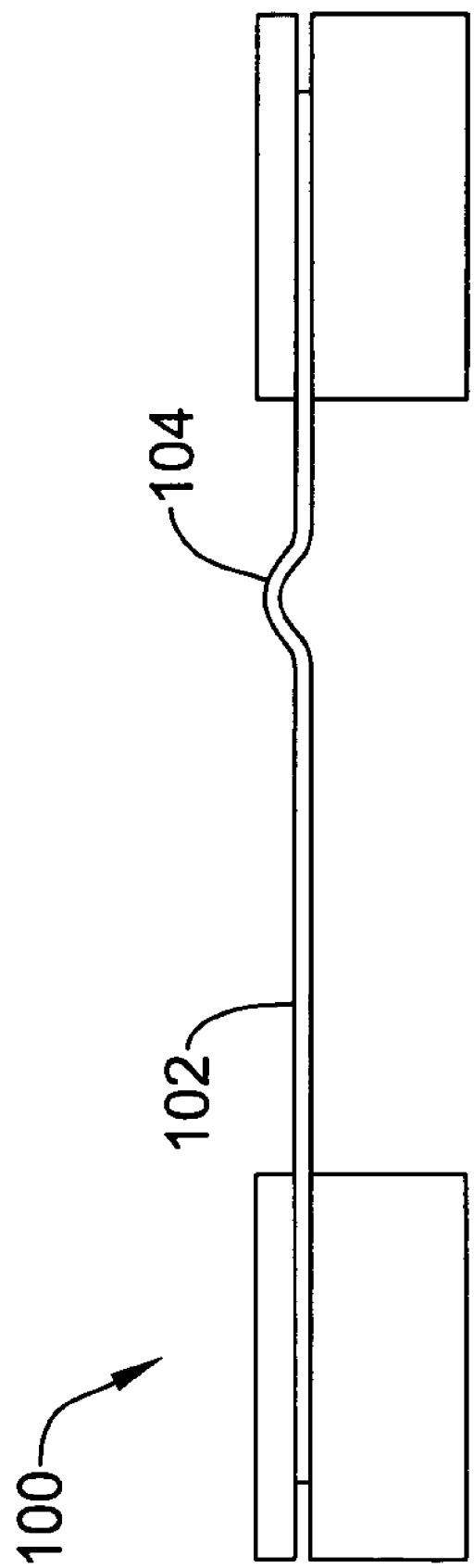
FIG. 2 is a plan view of a prior art support system for processing a flat stent with a partially processed stent therein.
Figure 3:
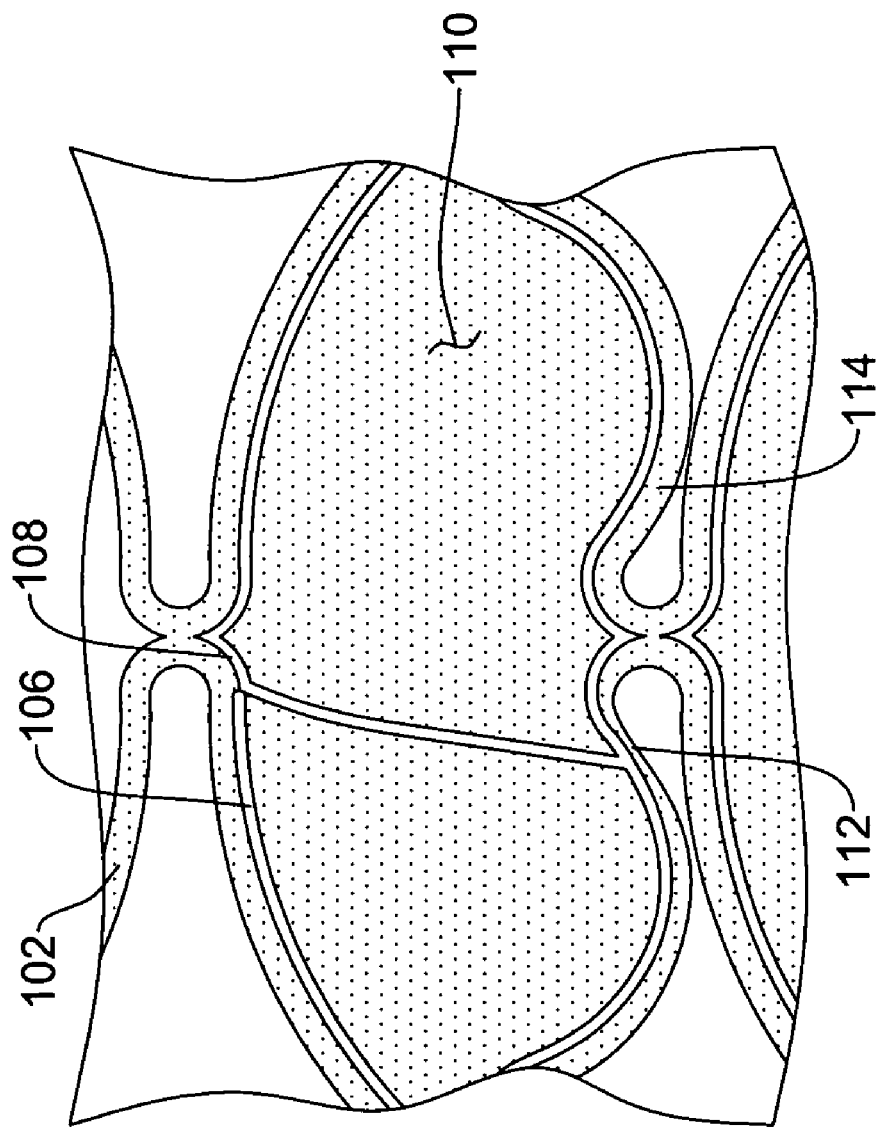
FIG. 3 is top view of a piece of material processed according to a prior art method.

FIG. 1 is a diagrammatic plan view of a prior art support system 100 for processing a flat stent. Support system 100 fixes stent precursor 102 in place for processing. Support system 100 may be a pair of clamps. Processing the stent precursor by laser-cutting and stress relieving the stent precursor, for example, may distort the stent precursor. FIG. 2, which is a diagrammatic plan view of a prior art support system 100 with partially processed stent precursor 102 therein, illustrates one issue with this prior technique. The flat material may deflect during processing from the high tension forces of the support system and distort, creating an undesired bump 104. FIG. 3, which is a partial top view of stent precursor 102, illustrates another issue. The distortion created in the material causes the material to deflect laterally so that the laser does not create the desired geometry. For instance, kerf 106 does not match up with adjacent kerf 108 and the desired effect of removing window 110 is not reached. Further, the struts may be created with an (undesired) non-uniform geometry such as strut 112 being thinner than strut 114.

Figure 4:
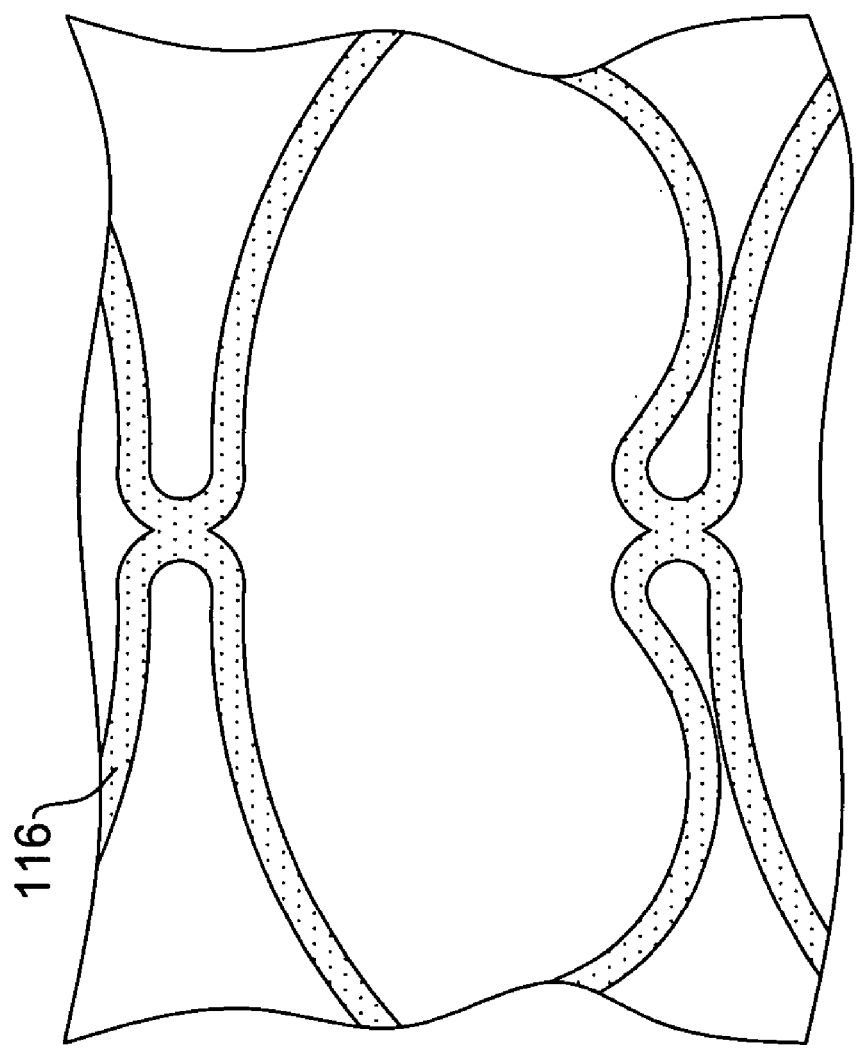
FIG. 4 is a top view of a piece of material processed according to an embodiment.

In contrast as illustrated in FIG. 4, which is a partial top view of a stent precursor 116 processed according to an embodiment, the struts have a uniform width and all windows have been cleanly removed.

Figure 5:
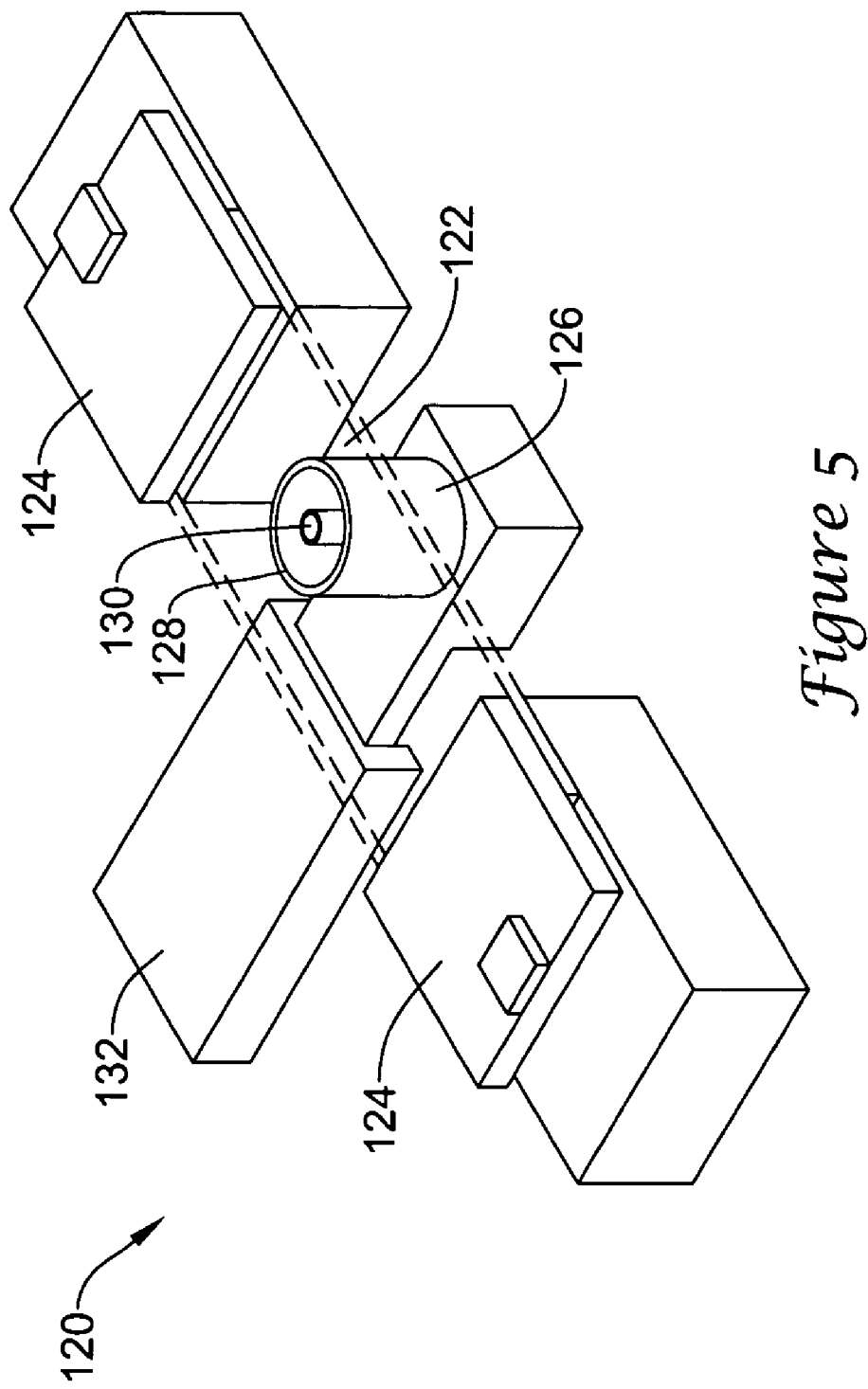
FIG. 5 is an apparatus for processing material according to an embodiment.

FIG. 5 is a diagrammatic perspective view of a center tower support system 120. Workpiece 122, illustrated in broken lines, is held in place by material holding component 124. Material holding component may be a pair of clamps, as illustrated, or may be any other mechanism suitable for fixing the workpiece 122 in place. Workpiece 122 may be fixed in tension as desired.

Center tower support 126 is disposed under the workpiece and includes an upper surface 128 for supporting the workpiece and a central lumen 130. In this embodiment, the center tower support is disposed on a cantilever arm 132 that may be moved laterally (i.e. along the x-axis and the y-axis) as desired. Alternatively, the center tower support may be disposed on a bridge or other suitable mechanism.

The center tower support provides several functions, several of which are illustrated here. The center tower support provides support to the workpiece against deflections that may be caused, for example, by gravity or by the cutting action of the cutting instrument. The center tower support may provide a datum that can be used during the cutting process. As discussed below in further detail, the center tower support may be used to provide cooling fluid to the workpiece and to evacuate scrap from the workpiece.

Figure 6:
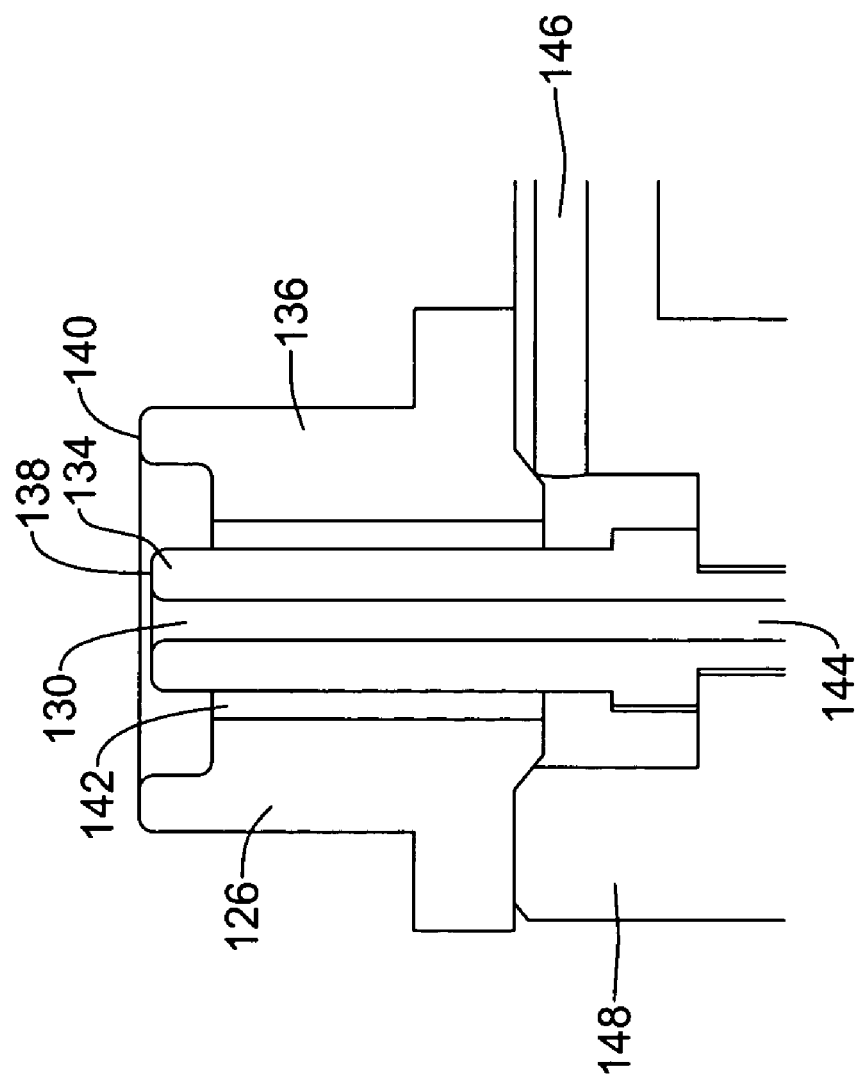
FIG. 6 is a cross-sectional plan view of a center tower support according to an embodiment.

FIG. 6 is a partial cross-sectional diagrammatic view of center tower support 126, which consists of inner tower 134 and outer tower 136. Both inner tower 134 and outer tower 136 are cylindrical and have annular upper surface 138 and 140, respectively. In alternative embodiments, either or both of the inner and outer towers may have a different shape. For example, outer tower 136 may have an oblong or rectangular cross-sectional shape. In one contemplated embodiment, center tower support comprises a single tower having an annular upper surface. In the embodiment of FIG. 6, inner tower 134 defines center lumen 130 and inner tower 134 and outer tower 136 together define an annular lumen 142. Center lumen 130 may be fluidly attached to a fluid source or an evacuation lumen through bottom lumen 144 or other suitable mechanism. Likewise, annular lumen 142 may be attached to a fluid source or an evacuation lumen through side lumen 146 or other suitable mechanism. Upper surfaces 138 and 140 may be raised or lowered relative to each other to change the profile of the upper support surface. This may be done, for example, to change the amount or direction of the fluid flow, as illustrated below. For example, inner tower 134 may be threadably inserted into support arm 148, outer tower 136 may be raised or lowered by the insertion or removal of shims or washers, or other suitable mechanisms may be used.

Figure 7:
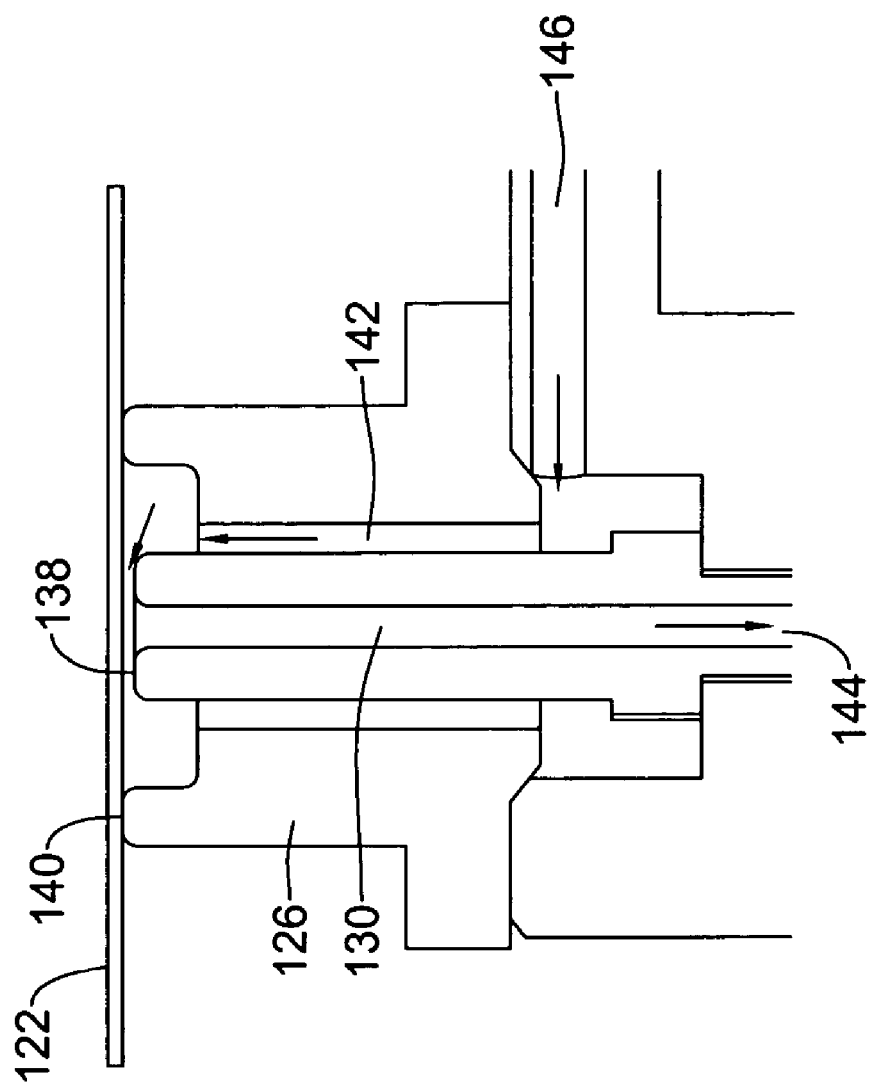
FIG. 7 is a diagram depicting a method of use of a center tower support.

FIG. 7 is a partial cross-sectional diagrammatic view of center tower support 126 in a particular configuration. Upper surface 140 is positioned proximate to the workpiece 122 and upper surface 138 is positioned at a lower level. Fluid may then be introduced through lumen 146, up through annular lumen 142 and evacuated down through center lumen 130 and out through lumen 144, as illustrated by the arrows.

Figure 8:
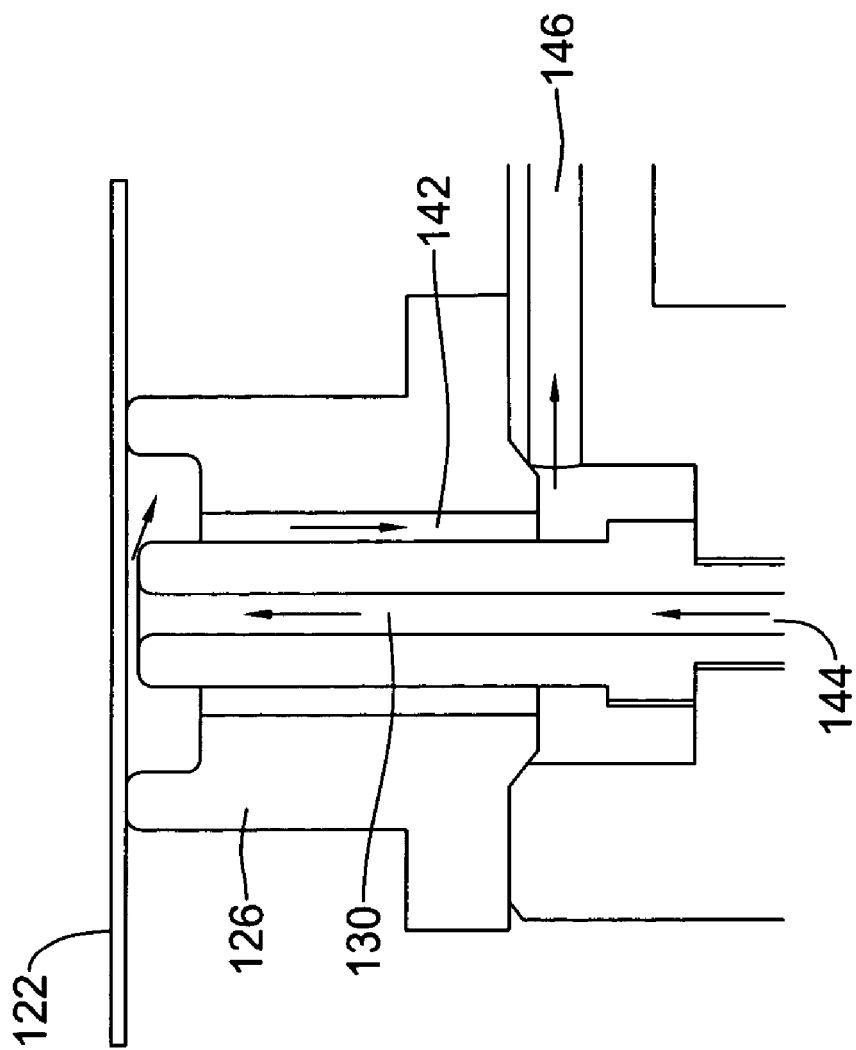
FIG. 8 is a diagram depicting a method of use of a center tower support.

FIG. 8 is a partial cross-sectional diagrammatic view of center tower support 126 in essentially the same relative configuration as in FIG. 7. However, here fluid is introduced through lumen 144 and up through the center lumen. The fluid is then evacuated through lumen 142 and out lumen 146, as illustrated by the arrows.

Figure 9:
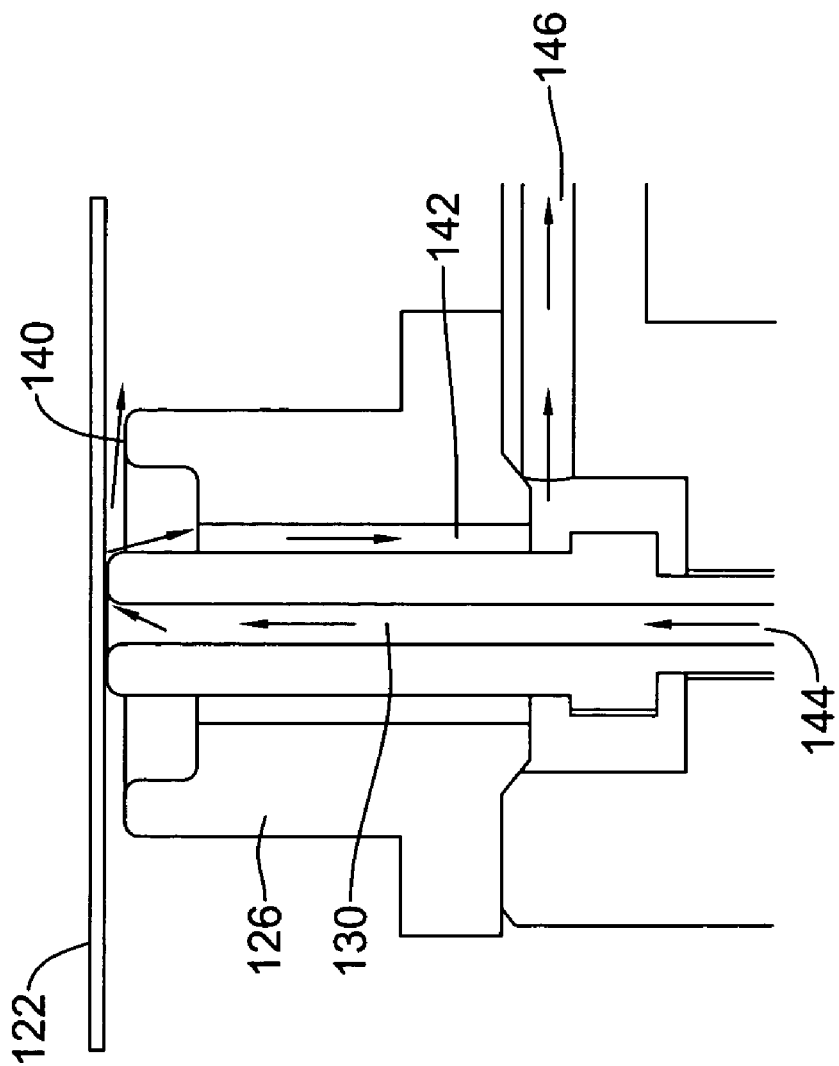
FIG. 9 is a diagram depicting a method of use of a center tower support.

FIG. 9 is a partial cross-sectional diagrammatic view of center tower support 126 in another configuration. Upper surface 138 is positioned slightly away from workpiece 122 and upper surface 140 is positioned at a lower level. As illustrated by the arrows, fluid is introduced through lumen 144 and up through center lumen 130. The fluid is then evacuated through two paths—down through annular lumen 142 and out lumen 146 and across upper surface 140. This configuration is an example of a liquid bearing surface where only the liquid is in contact with the workpiece.

Figure 10:
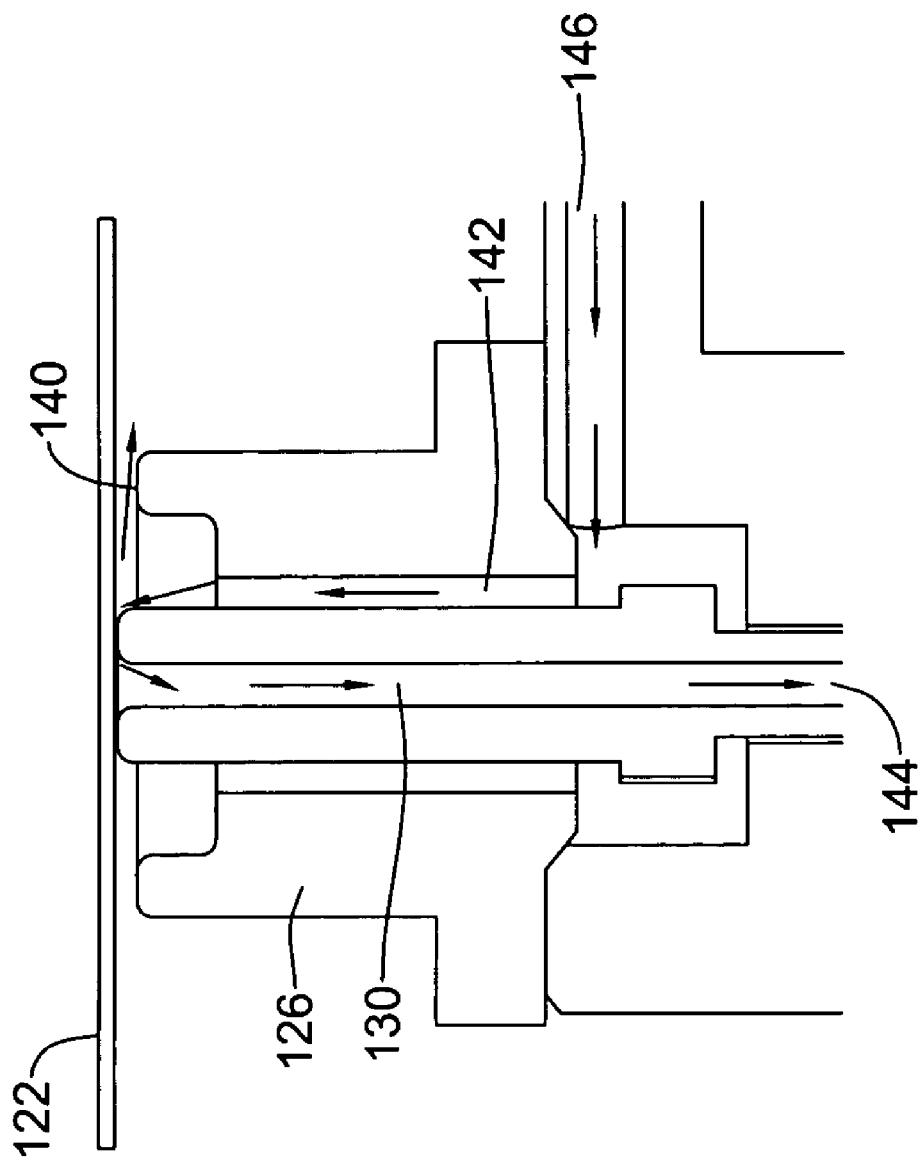
FIG. 10 is a diagram depicting a method of use of a center tower support.

FIG. 10 is a partial cross-sectional diagrammatic view of center tower support 126 in a configuration similar to that of FIG. 9 but illustrating an alternative flowpath. Fluid is introduced through lumen 146 and up through annular lumen 142. The fluid is then evacuated through center lumen 130 and outwardly across upper surface 140. The configurations depicted in FIGS. 7 through 10 are illustrative and other configurations may be used.

Figure 11:
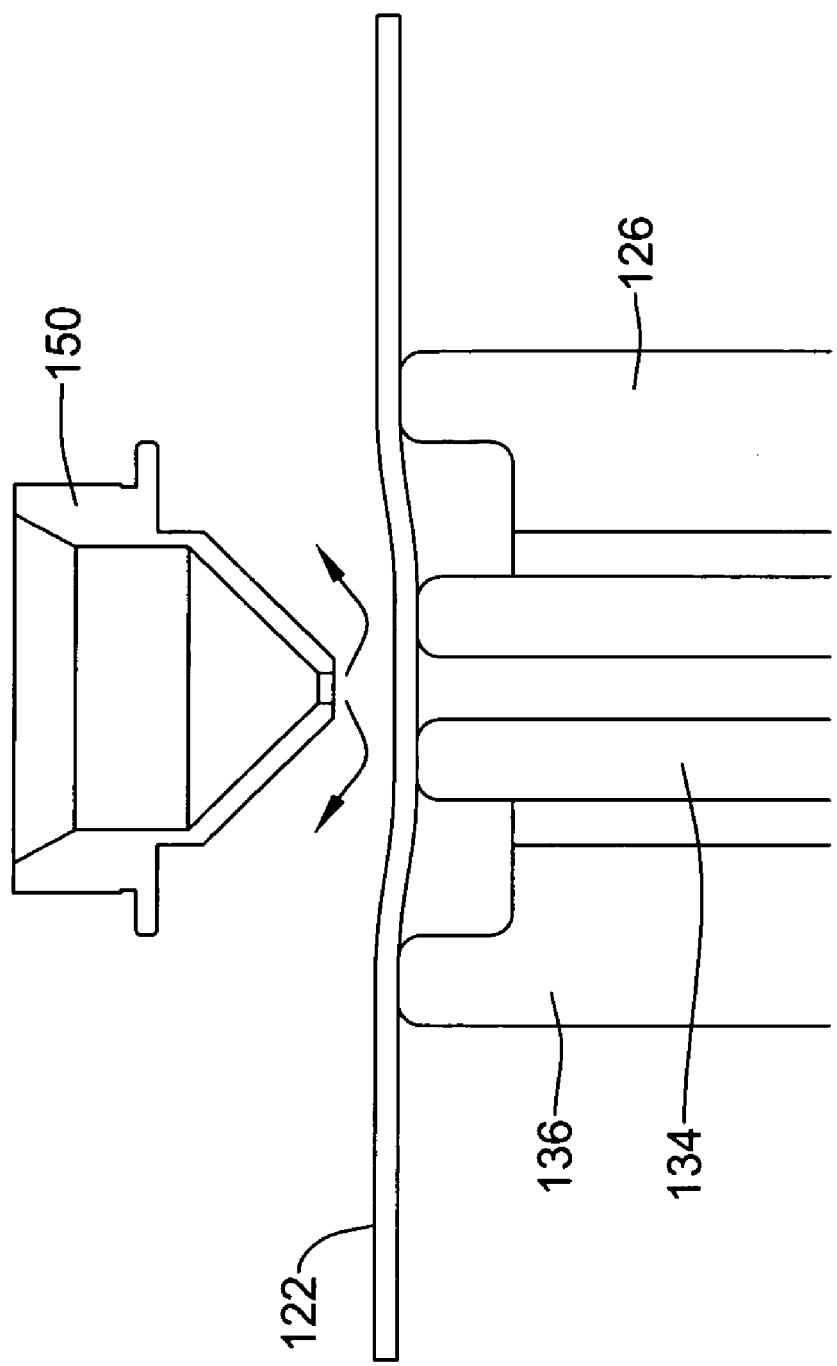
FIG. 11 is a cross-sectional view depicting a center tower support in use.

FIG. 11 is a partial cross-sectional diagrammatic view of center tower support 126 supporting workpiece 122 against the forces from the assist gases from a cutting nozzle 150. In this configuration, the center tower support permits only a slight bending during the cutting operation. In other configurations, the bending permitted could be lesser or greater. The bending permitted can be adjusted by adjusting the relative heights of inner tower 134 and outer tower 136, by the presence or absence of fluid flow, and by the amount of fluid flow, for example.

Figure 12:
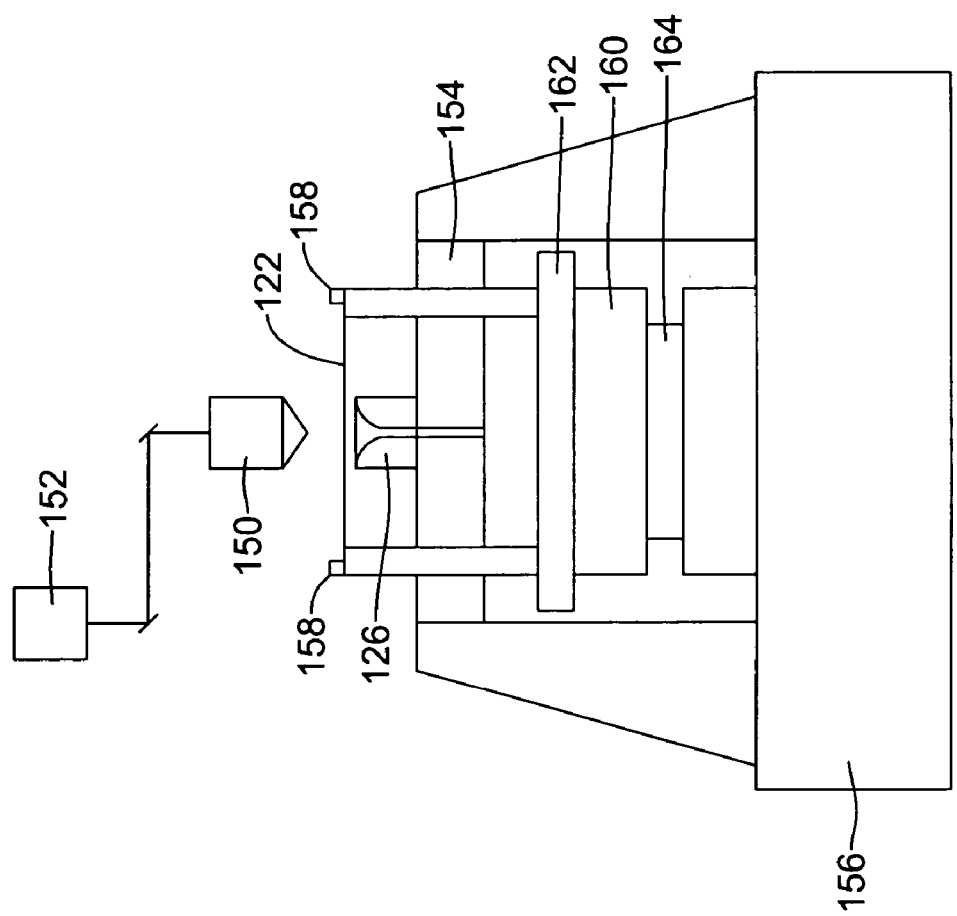
FIG. 12 is a diagrammatic view depicting an apparatus for processing material.

FIG. 12 is a diagrammatic plan view of a laser-processing system having a workpiece 122 disposed therein. In general operation, the laser cutting nozzle 150 and the center tower support 126 are fixed in position and workpiece 122 is moved during the processing operation. Cutting nozzle 150 is connected to laser source 152. A center tower support 126 is disposed on a bridge 154. Bridge 154 is fixed to a stationary object 156 that may be a granite or steel block for dimensional stability. Workpiece 122 is tensioned between clamps 158, which are fixed to a carriage 160. Carriage 160 provides for lateral movement along the x-axis and the y-axis. For example, carriage 160 may include a first linear actuator 162 that operates along the x-axis. Actuator 162 is mounted, in turn, on a second linear actuator 164 that operates along the y-axis. Other configurations are possible. For example, carriage 160 may include a rotary actuator as well as the two linear actuators or a rotary actuator and a single linear actuator. The center tower support may be as described above or may be an insert as described below.

In an alternate embodiment, the laser-processing system may have a fixed workpiece and a movable cutting nozzle and center tower support. The cutting nozzle and center tower support may be mechanically fixed to each other or may merely be synchronized through the electronic controls system. For example, the cutting nozzle may be mounted on one tine of a cantilevered fork and the center tower support may be mounted on another such that the system can provide the nozzle on the opposite side of the workpiece from the center tower support while mechanically ensuring synchronicity.

Figure 13:
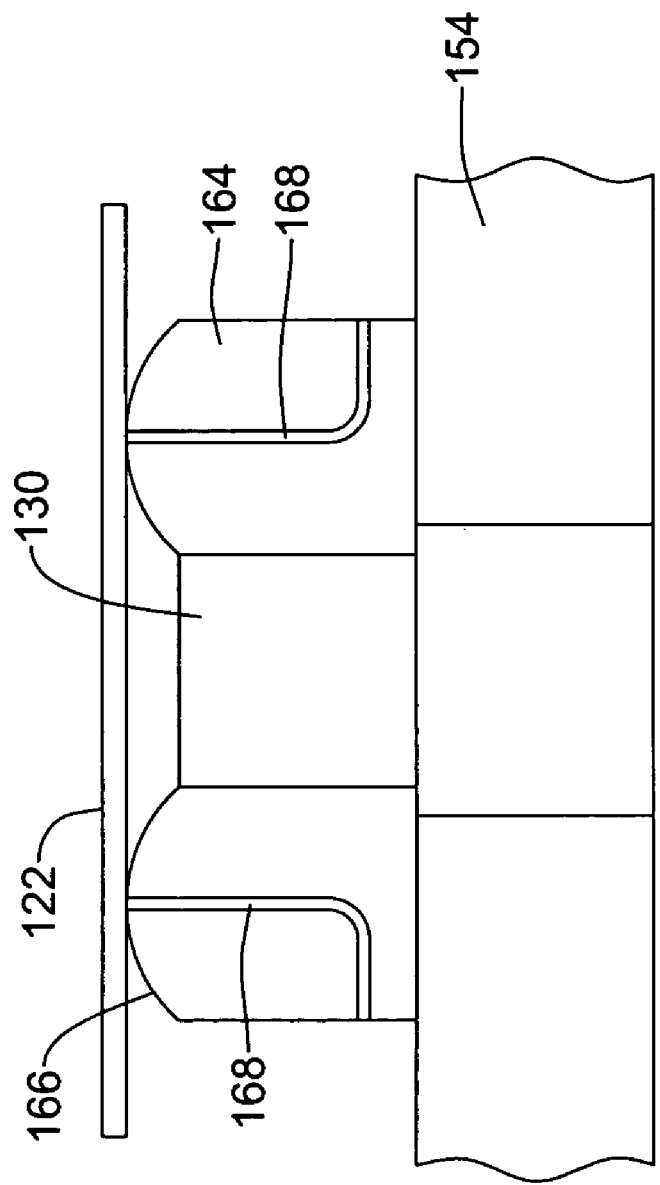
FIG. 13 is a cross-sectional view depicting an insert.

FIG. 13 is a partial diagrammatic cross-sectional view of an insert 164 according to the invention. Insert 164 is disposed on bridge 154 and supports a workpiece 122. Insert 164 may be threadably fastened to bridge 154. Insert 164 has an annular, crowned upper surface 166. The cross-sectional profile of upper surface 166 is illustrative and upper surface 166 may have an alternate profile. For example, upper surface 166 may have a flatter profile or it may have a planar ring-shaped surface with rounded inner and outer edges. Insert 164 includes a plurality of fluid delivery lumens 168 that have exit orifices disposed at upper surface 166. While only two lumens are illustrated in this cross-sectional view, it should be understood that lumens 168 are disposed at intervals about the insert. There may be, for example, 6, 8, 9, 12, or other suitable number of lumens disposed about the insert, each having a fluid exit orifice on upper surface 166. These lumens may be disposed at regular intervals. When fluid is provided through these lumens, a fluid bearing surface is formed between the upper surface of the insert and the workpiece. The insert may thereby support the workpiece without actually touching it. The fluid is evacuated over the inner and outer edges of the insert. The insert includes a central lumen 130 sized to receive scrap cut from the workpiece. For applications such as cutting stent precursors, a lumen diameter of between about 1 and 5 mm may be desired. Of course, other diameters may be selected as well. The insert may be made from any suitable material, including ceramics, stainless steels, graphalloy, DELRIN AF (acetal resin), TEFLON AF (amorphous fluoropolymer), or sintered ceramics or metals.

Figure 14:
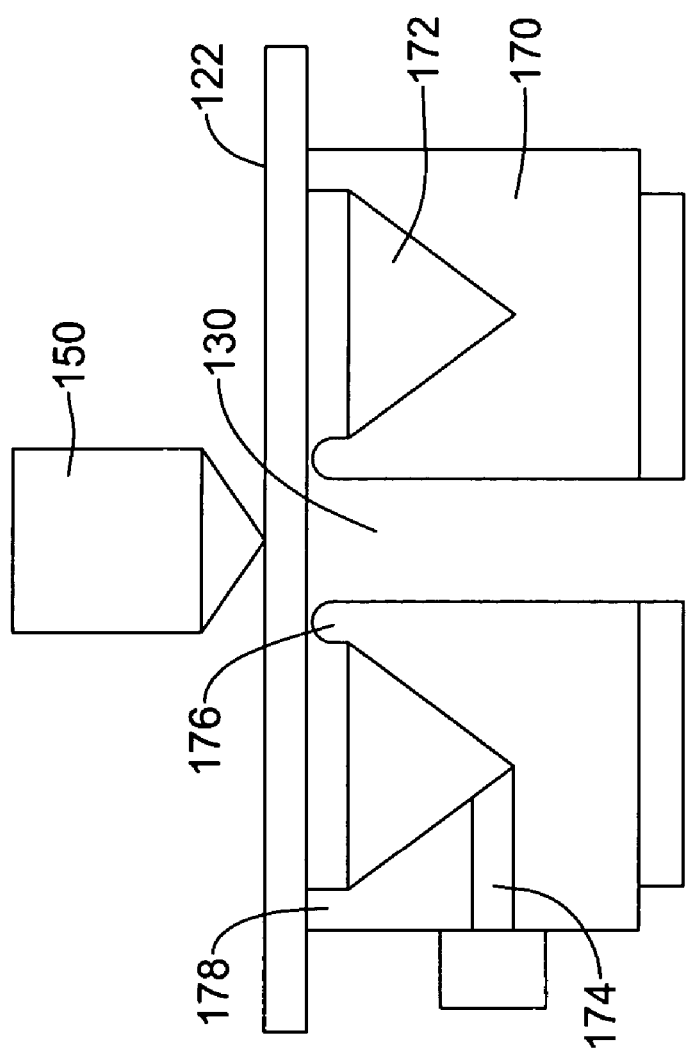
FIG. 14 is a cross-sectional view depicting an insert.

An alternative insert configuration is depicted in FIG. 14, which is a partial diagrammatic cross-sectional view thereof. Insert 170 defines a weir 172 that is filled with fluid through lumen 174 to create a liquid bearing surface. Insert 170 includes a central lumen 130 through which scrap and/or fluid may be evacuated. The weir surface is defined by inner wall 176 and outer wall 178, which may be adjustable or machinable to different heights to direct and optimize the fluid flow. In this configuration, inner wall 176 is slightly lower than outer wall 178 to direct the fluid flow to the center lumen. A needle valve (not depicted) or other suitable mechanism may be used to control the fluid flow and optimize back pressure.

Figure 15:
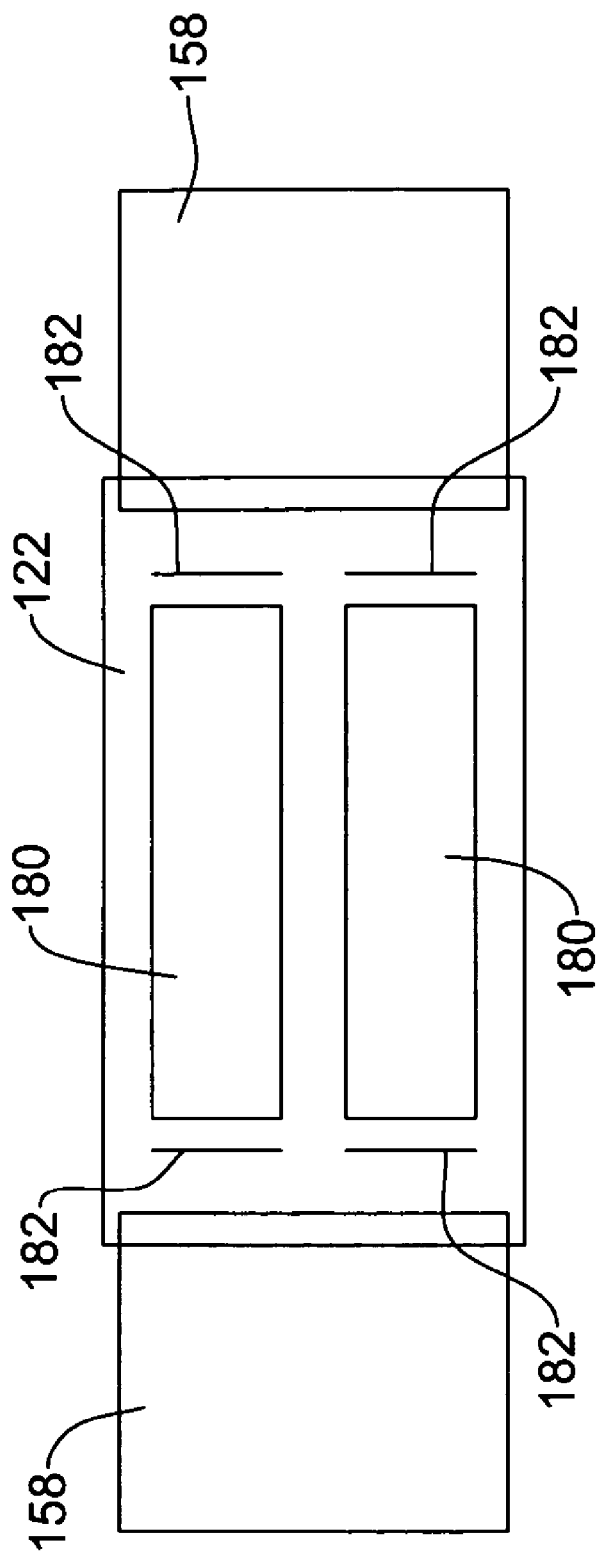
FIG. 15 is a top view depicting a method of processing material.

FIG. 15 is a top diagrammatic view of workpiece 122 in an alternate processing configuration. Workpiece 122 is tensioned between clamps 158 and includes two areas 180 to be formed into parts. Slits 182 are formed in the workpiece normal to the tension force prior to processing. Further, the direction of areas 180 is oriented relative to the tension to minimize deformation. For example, in this embodiment, the part areas are oriented so that the longer dimension is parallel to the tension forces. This processing configuration is suitable for use with any of the systems described herein.

Those skilled in the art will recognize that the present invention may be manifested in a variety of forms other than the specific embodiments described and contemplated herein. Accordingly, departure in form and detail may be made without departing from the scope and spirit of the present invention as described in the appended claims.

What is claimed is:

1. An apparatus for flat laser processing, comprising:
   a material holding component for holding a workpiece having a first surface opposite a second surface;
   a center tower support movable relative to the material holding component, the center tower support having an upper surface positionable proximate the second surface to provide support, said center tower support comprising an inner tower and an outer tower together defining a first lumen and a second lumen; and
   a fluid source which provides fluid flow between the first lumen and the second lumen, said fluid flow being across an upper surface of the central tower support.

2. The apparatus of claim 1, wherein the material holding component comprises a pair of clamps.

3. The apparatus of claim 2, wherein the pair of clamps are configured to hold the workpiece in tension.

4. The apparatus of claim 1, further comprising a beam delivery system for delivering a cutting beam to the workpiece.

5. The apparatus of claim 4, wherein the center tower support is attached to the beam system.

6. The apparatus of claim 1, wherein the center tower support is attached to a bridge fixed to a stationary item.

7. The apparatus of claim 1, wherein the center tower support is attached to a cantilever support arm.

8. The apparatus of claim 1, wherein the center tower support comprises a center lumen.

9. The apparatus of claim 8, wherein the center lumen is sized to receive scrap pieces from the workpiece.

10. The apparatus of claim 9, wherein the center lumen has a diameter of between about 1 and 5 mm.

11. The apparatus of claim 1, wherein the center tower support comprises
    an outer tower having an annular upper surface and an orifice therein, the outer tower having a cavity therein fluidly connected to the upper surface orifice and
    an inner tower having an annular upper surface and an orifice therein, the outer tower having a cavity therein fluidly connected to the upper surface orifice, the inner tower disposed in the cavity of the outer tower,
    the center tower support upper surface comprises the outer tower upper surface and the inner tower upper surface.

12. The apparatus of claim 11, wherein the center tower support comprises a fluid input port fluidly connected to the outer tower cavity and a drain fluidly connected to the inner tower cavity.

13. The apparatus of claim 11, wherein the inner tower can be raised or lowered relative to the outer tower.

14. The apparatus of claim 11, wherein the outer tower can be raised or lowered relative to the inner tower.

15. The apparatus of claim 11, wherein the center tower support comprises a fluid input port fluidly connected to the inner tower cavity and a drain fluidly connected to the outer tower cavity.

16. The apparatus of claim 1, wherein the center tower support includes a mechanism to provide a liquid bearing surface at the upper surface.

17. The apparatus of claim 16, wherein the center tower support includes a weir and wherein the weir is filled with a fluid to create the liquid bearing surface.

18. The apparatus of claim 16, further including a removable insert, the removable insert including the upper surface.

19. The apparatus of claim 18, wherein the removable insert comprises a material selected from the group consisting of ceramic, steel, graphite alloy, acetal resin, and amorphous fluoropolymer.

20. The apparatus of claim 16, wherein the upper surface is annular and crowned.

21. The apparatus of claim 20, wherein the upper surface includes a plurality of fluid exit lumens at an apex of the upper surface whereby a liquid bearing surface is formed at the upper surface when the upper surface is positioned proximate the workpiece and fluid is emitted from the plurality of fluid exit lumens.

22. The apparatus of claim 20, wherein the central lumen has a diameter of between 1 and 5 mm.

23. The apparatus of claim 20, wherein the weir is defined by an inner wall and an outer wall.

24. The apparatus of claim 23, wherein the inner wall defines the central lumen.

25. The apparatus of claim 23, wherein the inner wall has a height that is higher than the height of the outer wall such that fluid flow may be directed outwardly.

26. The apparatus of claim 23, wherein the inner wall has a height that is lower than the height of the outer wall such that fluid flow may be directed inwardly.

27. The apparatus of claim 23, further comprising a fluid inlet lumen fluidly connected to the weir.

28. The apparatus of claim 27, further comprising a needle valve disposed in the fluid inlet lumen.

29. The apparatus of claim 23 wherein the height of the inner wall is adjustable relative to the height of the outer wall.

30. The apparatus of claim 29 further comprising a threaded adjustment between the inner and outer walls.

31. The apparatus of claim 1, further comprising an arm, wherein the center tower support is disposed on the arm.

32. The apparatus of claim 31, wherein the am is configured to move along two axes.

33. The apparatus of claim 31, wherein the arm is cantilevered and the support is disposed proximate a free end of the arm.

34. A method of laser processing a flat medical component, comprising the steps of:
   providing the flat medical component;
   fixing the flat medical component in tension;
   providing a cutting nozzle;
   providing a center tower support having an upper surface and a central lumen;
   disposing the center tower support under the flat medical component and positioning the upper surface to provide support to the flat medical component against the action of the cutting nozzle;
   creating a fluid bearing surface between the center tower support and the flat medical component;
   cutting the flat medical component by operating and moving the cutting nozzle relative to the flat medical component; and
   ensuring the position of the center tower support such that the central lumen is under the cutting nozzle during the step of cutting the flat medical component.

35. The method of claim 34 further comprising the step of providing a plurality of slits in the flat medical component normal to the tension.

36. The method of claim 34 further comprising the step of creating a weir to support the flat medical component.

37. The method of claim 34 further comprising the steps of:
   cutting scrap from the flat medical component; and
   evacuating the scrap through the central lumen.

38. The method of claim 34 further comprising the steps of:
   holding the flat medical component stationary; and
   moving the cutting nozzle and the center tower support.

39. The method of claim 34 further comprising the steps of:
   holding the cutting nozzle and the center tower support stationary; and
   moving the flat medical component.

40. The method of claim 34 further comprising the step of providing fluid through the center tower support to the flat medical component.

41. The method of claim 40 further comprising the step of cooling the flat medical component with fluid.

42. The method of claim 40 further comprising the step of providing fluid through an annular lumen of the center tower support.

43. The method of claim 42 further comprising the step of evacuating the fluid through the central lumen of the center tower support.

44. The method of claim 42 further comprising the step of evacuating the fluid outwardly from the center tower support.

45. The method of claim 40 further comprising the step of providing fluid through the central lumen of the center tower support.

46. The method of claim 45 further comprising the step of evacuating the fluid through an annular lumen of the center tower support.

47. The method of claim 45 further comprising the step of evacuating the fluid outwardly from the center tower support.

* * * * *

UNITED STATES PATENT AND TRADEMARK OFFICE
CERTIFICATE OF CORRECTION

PATENT NO. : 7,589,297 B2 Page 1 of 1
APPLICATION NO. : 11/297499
DATED : September 15, 2009
INVENTOR(S) : Shedlov et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 881 days.

Signed and Sealed this

Twenty-first Day of September, 2010

David J. Kappos
*Director of the United States Patent and Trademark Office*